United States Patent
Kim et al.

(10) Patent No.: US 12,128,384 B2
(45) Date of Patent: Oct. 29, 2024

(54) CATALYST FOR NON-OXIDATIVE DIRECT CONVERSION OF METHANE AND PREPARATION METHOD FOR SAME

(71) Applicant: KOREA RESEARCH INSTITUTE OF CHEMICAL TECHNOLOGY, Daejeon (KR)

(72) Inventors: Yong Tae Kim, Daejeon (KR); Sung Woo Lee, Daejeon (KR); Seung Ju Han, Daejeon (KR); Seok Ki Kim, Daejeon (KR); Hyun Woo Kim, Daejeon (KR)

(73) Assignee: KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 285 days.

(21) Appl. No.: 17/278,542

(22) PCT Filed: Sep. 24, 2019

(86) PCT No.: PCT/KR2019/012390
§ 371 (c)(1),
(2) Date: Mar. 22, 2021

(87) PCT Pub. No.: WO2020/091227
PCT Pub. Date: May 7, 2020

(65) Prior Publication Data
US 2021/0346871 A1 Nov. 11, 2021

(30) Foreign Application Priority Data
Oct. 31, 2018 (KR) .................... 10-2018-0132422

(51) Int. Cl.
| | |
|---|---|
| *B01J 23/745* | (2006.01) |
| *B01J 21/08* | (2006.01) |
| *B01J 35/02* | (2006.01) |
| *B01J 35/10* | (2006.01) |
| *B01J 35/40* | (2024.01) |
| *B01J 35/61* | (2024.01) |
| *B01J 37/00* | (2006.01) |
| *B01J 37/04* | (2006.01) |
| *C07C 2/24* | (2006.01) |

(52) U.S. Cl.
CPC .............. *B01J 23/745* (2013.01); *B01J 21/08* (2013.01); *B01J 35/40* (2024.01); *B01J 35/612* (2024.01); *B01J 37/0036* (2013.01); *B01J 37/0081* (2013.01); *B01J 37/04* (2013.01); *C07C 2/24* (2013.01); *C07C 2523/745* (2013.01)

(58) Field of Classification Search
CPC ........ B01J 23/745; B01J 21/08; B01J 35/023; B01J 35/1009; B01J 37/0036; B01J 37/0081; B01J 37/04; C07C 2/24
See application file for complete search history.

(56) References Cited

U.S. PATENT DOCUMENTS

| | | |
|---|---|---|
| 2014/0336432 A1 | 11/2014 | Bao et al. |
| 2016/0362351 A1 | 12/2016 | Nagaki et al. |
| 2018/0296974 A1 | 10/2018 | Wachsman et al. |

FOREIGN PATENT DOCUMENTS

| | | |
|---|---|---|
| CN | 104557423 A | 4/2015 |

OTHER PUBLICATIONS

Benedicte, "Direct Nonoxidative Conversion of Methane to C2 Hydrocarbons, Aromatics and Hydrogen", Norwegian University of Science and Technology, Jun. 9, 2016, pp. 1-64 (Provided by Applicant).*
Blast Furnace and its Design—IspatGuru (2014).*
International Search Report dated Jan. 21, 2020, in connection with corresponding International Patent Application No. PCT/KR2019/012390, citing the above references.
Benedicte, Hovd. "Direct Nonoxidative Conversion of Methane to C2 Hydrocarbons, Aromatics and Hydrogen", Norwegian University of Science and Technology, Jun. 9, 2016, pp. 1-64.
Deangelis, Michale T., et al., "Sol-gel synthesis of nanocrystalline fayalite(Fe2SiO4)", American Mineralogist, 2012, vol. 97 No. 4, pp. 653-656.
Xiaoguang Guo et al. "Direct, Nonoxidative Conversion of Methane to Ethylene, Aromatics, and Hydrogen", Science, 2014, vol. 344, pp. 616-619, Cited in the Specification.
Mann Sakbodin et al. "Hydrogen-Permeable Tubular Membrane Reactor: Promoting Conversion and Product Selectivity for Non-Oxidative Activation of Methane over an Fe©SiO2 Catalyst" Angewante Chemie, 2016, vol. 128, pp. 16383-16386, Cited in the Specification.

* cited by examiner

*Primary Examiner* — Yong L Chu
(74) *Attorney, Agent, or Firm* — Hauptman Ham, LLP (57) ABSTRACT

The present disclosure relates to a catalyst for direct non-oxidative conversion of methane and a method of preparing the same, and more particularly to a method of preparing a catalyst for direct nonoxidative conversion of methane, in which a catalyst optimized for the direct conversion reaction of methane can be easily prepared without precise control of the reaction conditions for direct conversion of methane, thereby simultaneously maximizing the catalytic reaction rate and minimizing coke formation, and exhibiting stable catalytic performance even after long-term operation, and to a catalyst for direct nonoxidative conversion of methane prepared using the above method.

9 Claims, 4 Drawing Sheets

CATALYST FOR NON-OXIDATIVE DIRECT CONVERSION OF METHANE AND PREPARATION METHOD FOR SAME

CROSS-REFERENCE TO RELATED APPLICATION

The present application is a national stage filing under 35 U.S.C § 371 of PCT application number PCT/KR2019/012390 filed on Sep. 24, 2019, which is based upon and claims the benefit of priorities to Korean Patent Application No. 10-2018-0132422, filed on Oct. 31, 2018, in the Korean Intellectual Property Office, which are incorporated herein in their entireties by reference.

TECHNICAL FIELD

The present disclosure relates to a catalyst for direct nonoxidative conversion of methane and a method of preparing the same, and more particularly to a catalyst suitable for directly converting methane, which is a main component of natural gas, in an anaerobic or oxygen-free atmosphere, and a method of preparing the same.

BACKGROUND ART

In recent years, efforts to convert methane ($CH_4$), which may be obtained from natural gas, shale gas, and the like, into value-added products such as transportation fuels or chemical materials have been continually made. Representative examples of value-added products capable of being obtained from methane include light olefins (ethylene, propylene, butylene, etc.), and MTO (methanol to olefins) technology, in which synthesis gas ($H_2$+CO) obtained through methane reforming is prepared into light olefins via methanol, and FTO (Fischer-Tropsch to olefins) technology, in which light olefins are directly produced from synthesis gas, are known as the most feasible techniques. However, in the case of technology that produces value-added products via synthesis gas, $H_2$ or CO is additionally required in order to remove the O atom from CO, which decreases the efficiency of use of H or C atoms in the entire process.

Therefore, new technology capable of directly converting methane into value-added products without using synthesis gas is required. In order to directly convert methane into a value-added product, it is first necessary to activate methane by cleaving C—H bonds (434 kJ/mol), which are strongly formed in methane. From this aspect, thorough research into oxidative coupling of methane (OCM) technology, which activates methane using oxygen, has been conducted. However, the OCM reaction is still problematic because thermodynamically stable $H_2O$ and $CO_2$ are formed in large amounts due to the vigorous reactivity of $O_2$, and thus the efficiency of use of the H or C atoms is decreased.

With the goal of solving this problem, a technique for producing ethylene, aromatic compounds, etc. through direct conversion of methane under anaerobic or oxygen-free conditions has recently been developed. However, since the reaction takes place under high-temperature and high-pressure conditions due to the low reactivity of methane, the development of a catalyst therefor is essential. Based on the results of studies to date, the problem of a rapid decrease in catalytic activity due to deposition of carbon (coke) in the catalyst under high-temperature and high-pressure conditions has emerged as a key issue (Non-patent Documents 0001 and 0002).

Accordingly, U.S. Patent Application Publication No. 2014-0336432 discloses a method of performing nonoxidative conversion of methane including reacting a methane-containing methane material in the presence of a catalyst, in which, in order to suppress the deposition of carbon (coke) in the catalyst under high-temperature and high-pressure conditions, a metal element is doped in the lattice of the amorphous-molten-state material made of Si bound with at least one of C, N, and O, and in which the doping amount of the metal-lattice-doped catalyst is 0.01 wt % to 10 wt % based on the total weight of the catalyst. U.S. Patent Application Publication No. 2016-0362351 discloses a method for nonoxidative coupling of methane using a catalyst doped in the lattice of an amorphous-molten-state material made of B, Al, Si, Ti, Zr and Ge, in which a chemically active metal is bound with at least one of C, N and O.

Although the above literature proposes a catalyst in which coke formation is suppressed and the catalytic reaction rate is improved compared to a conventional catalyst for direct nonoxidative conversion of methane prepared through a sol-gel or impregnation method, there are problems in that no method or conditions for the preparation of a catalyst optimized for direct nonoxidative conversion of methane are mentioned, and an appropriate reactor for a radical reaction has to be additionally provided in order to simultaneously maximize the high catalytic reaction rate and minimize coke formation, and also in that the reaction conditions need to be precisely controlled depending on the type of catalyst that is applied to the nonoxidative conversion of methane, and, if the reaction conditions are not appropriate, the coke selectivity is also high with an increase in the conversion rate of methane, and thus the selectivity of hydrocarbon compounds, the production rate and the like decrease. Moreover, since there are many factors that affect the reaction, such as the location of the packing portion of the catalyst, the material of the reactor, the amount of impurities in the reaction system, and the purity of the methane material, it is difficult to control the selectivity of the hydrocarbon compounds, the production rate, and the like.

CITATION LIST

Patent Literature (Patent Document 1) U.S. Patent Application Publication No. 2014-0336432 (Publication date: Nov. 13, 2014)
(Patent Document 2) U.S. Patent Application Publication No. 2016-0362351 (Publication date: Dec. 15, 2016)

Non-Patent Literature (Non-Patent Document 1) X, Guo et al., Direct, Nonoxidative Conversion of Methane to Ethylene, Aromatics, and Hydrogen, Science, 344, 2014, 616-619
(Non-Patent Document 2) Mann Sakbodin et al., Hydrogen-Permeable Tubular Membrane Reactor: Promoting Conversion and Product Selectivity for Nonoxidative Activation of Methane over an FeVSiO2 Catalyst, Angew. Chem. 2016, 128, 16383-16386

DISCLOSURE

Technical Problem

The present disclosure has been made keeping in mind the problems encountered in the related art, and an objective of the present disclosure is to provide a method of preparing a catalyst for direct nonoxidative conversion of methane, in which a catalyst optimized for the direct conversion reaction of methane may be easily prepared without precise control of the reaction conditions for direct conversion of methane, thereby simultaneously maximizing the catalytic reaction rate and minimizing coke formation, and exhibiting stable catalytic performance even after long-term operation, and a catalyst for direct nonoxidative conversion of methane prepared using the above method.

Technical Solution

In order to accomplish the above objective, an embodiment of the present disclosure provides a method of preparing a catalyst for direct nonoxidative conversion of methane, including: (a) mixing fayalite with a catalyst carrier compound to obtain a mixture, which is then pulverized for 6 hours to 18 hours at a speed of 100 rpm to 300 rpm in an inert atmosphere using a ball mill; (b) placing the pulverized mixture in a reaction furnace and then performing melting to obtain a melt; and (c) solidifying the obtained melt.

In a preferred embodiment of the present disclosure, the melting in step (b) is performed through heating to a temperature of 1,200° C. to 2,000° C. at a heating rate of 6° C./min or more.

In a preferred embodiment of the present disclosure, the height-to-diameter ratio of the reaction furnace in step (b) is 0.2-3.

In a preferred embodiment of the present disclosure, in step (a), fayalite is mixed in an amount of 0.1 parts by weight to 20 parts by weight based on 100 parts by weight of the catalyst carrier compound.

In a preferred embodiment of the present disclosure, the solidifying in step (c) is performed through rapid cooling at 0.2° C./s to 150° C./s.

In a preferred embodiment of the present disclosure, after step (a), steps (b) and (c) are repeatedly performed two or more times.

In a preferred embodiment of the present disclosure, the catalyst carrier compound is at least one selected from the group consisting of silica, alumina, titania, zirconia, and silicon carbide.

Another embodiment of the present disclosure provides a catalyst for direct nonoxidative conversion of methane, prepared using the method described above and including a catalyst carrier including a catalyst carrier compound and iron dispersed and supported in the form of nanoparticles having an average diameter of 5 nm or less on the catalyst carrier.

In another preferred embodiment of the present disclosure, the iron is supported in an amount of 0.1 wt % to 10.0 wt % based on the total weight of the catalyst.

In another preferred embodiment of the present disclosure, the catalyst carrier is in a molten crystalline state.

In another preferred embodiment of the present disclosure, the catalyst carrier compound is at least one selected from the group consisting of silica, alumina, titania, zirconia, and silicon carbide.

Advantageous Effects

According to the present disclosure, there is an effect of providing a catalyst, which is capable of simultaneously maximizing the catalytic reaction rate without precise control of the reaction conditions for direct nonoxidative conversion of methane and minimizing coke formation, and can exhibit stable catalytic performance even after long-term operation, compared to a conventional catalyst for direct nonoxidative conversion of methane prepared through a sol-gel or impregnation method.

MODE FOR DISCLOSURE

Unless otherwise defined, all technical and scientific terms used herein have the same meanings as those typically understood by those skilled in the art to which the present disclosure belongs. Generally, the nomenclature used herein is well known in the art and is typical.

As used herein, when any part is said to "comprise" or "include" any element, this does not mean that other elements are excluded, and such other elements may be further included unless otherwise specifically mentioned.

An aspect of the present disclosure pertains to a method of preparing a catalyst for direct nonoxidative conversion of methane including (a) mixing fayalite with a catalyst carrier compound to obtain a mixture, which is then pulverized for 6 hours to 18 hours at a speed of 100 rpm to 300 rpm in an inert atmosphere using a ball mill, (b) placing the pulverized mixture in a reaction furnace and then performing melting to obtain a melt, and (c) solidifying the obtained melt.

More specifically, the method of preparing a catalyst for direct nonoxidative conversion of methane according to the present disclosure includes a step of performing micronization under specific conditions and a melting step in order to increase uniformity and dispersibility of the catalyst through micronization before the melting step and prevent the activity of the catalyst from deteriorating owing to reduction and sintering of the catalyst due to heat generated during the micronization process. Thereby, it is possible to easily provide a catalyst for direct nonoxidative conversion of methane, which is capable of simultaneously maximizing the catalytic reaction rate to form a product and minimizing coke formation, and may exhibit stable catalytic performance even after long-term operation.

Hereinafter, a detailed description will be given of a method of preparing a catalyst for direct nonoxidative conversion of methane according to the present disclosure with reference to the accompanying drawings.

Figure 1:
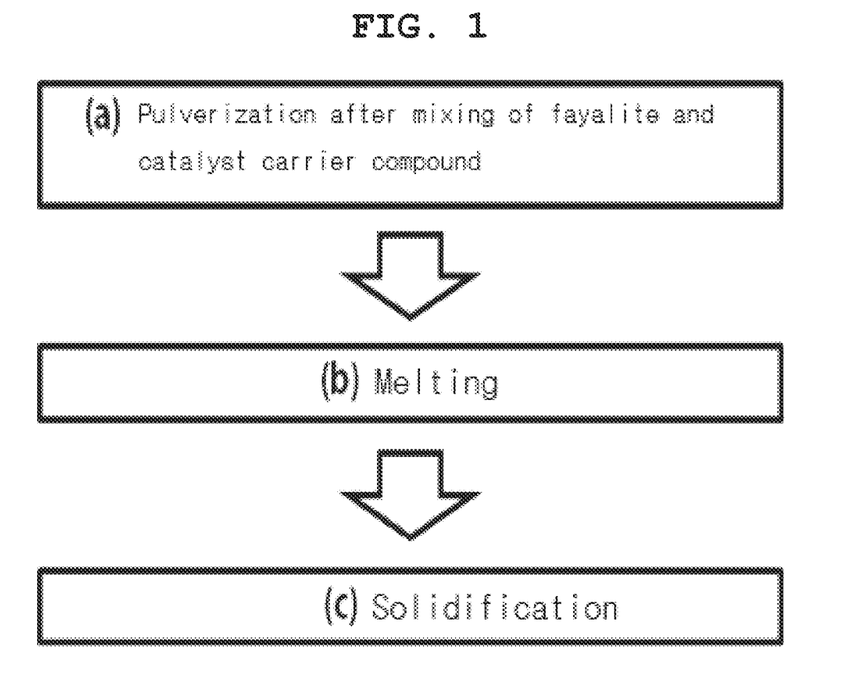
FIG. 1 is a flowchart showing a process of preparing a catalyst for direct nonoxidative conversion of methane according to the present disclosure.

FIG. 1 is a flowchart showing the process of preparing a catalyst for direct nonoxidative conversion of methane according to the present disclosure.

In the method of preparing a catalyst for direct nonoxidative conversion of methane according to the present disclosure, fayalite and a catalyst carrier compound are mixed and then pulverized for 6 hours to 18 hours at a speed of 100 rpm to 300 rpm using a ball mill [step (a)].

Here, fayalite ($Fe_2SiO_4$) is a silicate containing an iron component, and may be prepared using a silicon precursor and an iron precursor, or any commercially available example may be used without limitation.

In the preparation of fayalite, for example, fayalite may be obtained by dispersing a silicon precursor and an iron precursor in a solvent such as water or an alcohol and performing a sol-gel reaction such as hydrolysis and/or condensation.

Here, the solvent is not particularly limited, but water, alcohol, benzene, toluene, xylene, and mixtures thereof may be used, and the solvent is preferably used in an amount corresponding to 5 to 20 times the total weight of the silicon and iron precursors that are used. If the amount thereof is less than 5 times, the dispersion effect may be deteriorated, whereas if the amount thereof is greater than 20 times, the gelling process may be delayed.

Examples of the silicon precursor may include gaseous, liquid, and solid silicon precursors. Here, the liquid silicon precursor may be tetraethyl silicate, silicon tetrachloride, organosilane, etc., and the solid silicon precursor may be silica, silicon carbide, silicon nitride, etc.

Moreover, examples of the iron precursor may include iron chlorides such as $FeCl_2$, $FeCl_3$, etc., iron oxides such as FeO, $Fe_2O_3$, $Fe_3O_4$, etc., iron carbides such as $Fe_5C_2$, $Fe_3C$, etc., iron nitrides such as $Fe_2N$, $Fe_4N$, $Fe_7N_3$, etc., iron silicides such as $Fe_2SiO_4$, $Fe_2O_3 \cdot SiO_2$, etc., and iron silicate.

The sol-gel reaction of the reaction solution in which the silicon precursor and the iron precursor are dissolved may be performed at a temperature ranging from room temperature to 150° C. for 1 to 15 hours. If the reaction temperature is lower than room temperature, the gelling time may be prolonged, whereas if the reaction temperature exceeds 150° C., gelling may become excessive and the structure may collapse.

The reaction product thus obtained may be dried and fired to prepare fayalite ($Fe_2SiO_4$), and in order to prevent the reduction thereof, the reaction product may be dried at 20° C. to 80° C. for 1 hour to 24 hours in an inert atmosphere such as Ar, He, etc., and then fired at 500° C. to 1,000° C. for 1 hour to 5 hours in an inert atmosphere.

If the drying temperature is lower than 20° C. or the drying time is less than 1 hour, drying efficiency may not be good, whereas if the drying temperature is higher than 80° C. or the drying time exceeds 24 hours, the catalytic performance may be adversely affected. If the firing temperature is lower than 500° C. or the firing time is less than 1 hour, it may be difficult to remove reaction impurities, whereas if the firing time exceeds 5 hours, the catalytic performance may be adversely affected, and if the firing temperature is higher than 1,000° C., it may be difficult to perform micronization described below, and a sintering phenomenon may occur.

In addition, fayalite ($Fe_2SiO_4$) may be obtained by physically mixing an iron precursor such as $Fe_2O_3$, Fe, or the like and a silicon precursor such as $SiO_2$ or the like and performing a mechanical synthesis process such as heating at a high temperature. Thermodynamically, in the Fe—O system at a temperature of 570° C. or higher, FeO may be stably formed, and may react with a silicon precursor to form fayalite.

Thereafter, the fayalite is mixed with a catalyst carrier compound and then pulverized for 6 hours to 18 hours at a speed of 100 rpm to 300 rpm using a ball mill in an inert atmosphere such as Ar, He, etc. in order to prevent the reduction thereof.

The catalyst carrier compound that is mixed with the fayalite may be silica, alumina, titania, zirconia, or silicon carbide, and preferably silica, and fayalite may be mixed in an amount of 0.1 parts by weight to 20 parts by weight, and preferably 0.5 parts by weight to 10 parts by weight, based on 100 parts by weight of the catalyst carrier compound.

Here, if the amount of fayalite is less than 0.1 parts by weight based on 100 parts by weight of the catalyst carrier compound, the catalytic reaction rate cannot be maximized due to the small amount of the active component of the catalyst, and the density of the catalyst is low, so stable catalytic performance cannot be exhibited. On the other hand, if the amount thereof exceeds 20 parts by weight, the particle size of the iron particles, which is the active site of methane activation, may increase, and the amount thereof may also increase, undesirably increasing the rate of coke formation.

As described above, the mixture in which the fayalite and the catalyst carrier compound are mixed is micronized using a ball mill. There is no particular limitation on the ball mill device that is used to micronize the mixture of the fayalite and the catalyst carrier compound, and a typical ball mill device may be used.

The ball mill is used for pulverization for 6 hours to 18 hours at a speed of 100 rpm to 300 rpm in an inert atmosphere in order to prevent the reduction of fayalite and increase the effects of micronization and uniform mixing. When close contact between the fayalite and the catalyst carrier compound is increased using the ball mill, there is an effect of increasing the uniformity and density of the catalyst. If the rotational speed or time of the ball mill is less than 100 rpm or less than 6 hours, respectively, limitations may be imposed on controlling the particle size and the close contact between the particles during the micronization of the fayalite and the catalyst carrier, whereas if the rotational speed or time of the ball mill exceeds 300 rpm or 15 hours, respectively, there may occur a problem of deterioration of the activity of forming a product due to sintering of the catalyst carrier and the active metal.

The mixture thus micronized may have an average diameter of 60 μm or less, and preferably 50 nm to 50 μm. If the average diameter of the micronized mixture exceeds 60 μm, limitations may be imposed on controlling the close contact between the particles upon melting of the fayalite and the catalyst carrier, and ultimately, controlling the selective reduction of the iron particles in the fayalite and the particle size of the iron particles may be problematic.

Thereafter, the mixture micronized using the ball mill is placed in a reaction furnace and then melted to obtain a melt [step (b)], and the melt thus obtained is solidified [step (c)].

Here, the reaction furnace may be used without limitation, so long as the reaction furnace is made of a material having thermal stability at the melting temperature. If the height-to-diameter ratio of the reaction furnace is less than 0.2, it is difficult to uniformly melt the catalyst carrier and the catalytically active component, making it difficult to produce a uniform catalyst. On the other hand, if the height-to-diameter ratio of the reaction furnace exceeds 3, the reduction rate of the active metal of the catalyst may increase during melting, and the uniformity and density of the catalyst particles may tend to decrease when the melt is solidified through cooling.

The mixture placed in the reaction furnace may be melted at a temperature capable of completely melting the mixture, and the melting may be performed through heating to a temperature of 1,200° C. to 2,000° C. at a heating rate of 6° C./min or more, and preferably 6° C./min to 15° C./min, in air or in an inert atmosphere.

If the melting temperature is lower than 1,200° C., it is difficult to melt both the catalyst carrier and the catalytically active component, which may make it difficult to prepare a uniform catalyst. On the other hand, if the melting temperature exceeds 2,000° C., the catalyst carrier and the catalytically active component may evaporate and may thus be lost, which may make it difficult to prepare a uniform catalyst. Here, the melting time may be set sufficiently long so as to realize sufficient melting, and is preferably about 3 to 9 hours.

As such, the phase transition of the catalyst may be promoted depending on the melting rate, ultimately making it possible to prepare a high-density catalyst having high crystallinity. If the heating rate for melting is less than 6° C./min, there may occur problems of promoting the reduction of fayalite into a metal and lowering the uniformity and density of the catalyst.

Moreover, after melting, the solidification step may be performed through rapid cooling or natural cooling. The rapid cooling may be performed through gas cooling, water cooling, oil cooling, liquid nitrogen cooling, or the like, and preferably, rapid cooling is performed in the range of 0.2° C./s to 150° C./s. When the rapid cooling is performed in the above range, the uniformity of the catalyst may be improved by suppressing non-uniformity due to a difference in melting point between the active metal and the carrier component.

The gas in the gas cooling may be at least one selected from the group consisting of inflammable gas and air, and the oil in the oil cooling may be mineral oil, rapeseed oil, silicone oil, or the like.

In addition, the catalyst for direct nonoxidative conversion of methane according to the present disclosure is capable of further decreasing the pore volume of the catalyst by repeatedly performing the melting and solidification steps as described above. Here, the number of repetitions of the melting step and the solidifying step may be 2 or more, and specifically may be 2 to 5.

The catalyst for direct nonoxidative conversion of methane thus prepared is uniformly mixed with an inorganic binder, an organic binder, and water in order to granulate the same, thus obtaining a catalyst mixture, which is then molded to produce a catalyst-molded body.

The organic binder may include those useful in the art, and is not particularly limited, but it is preferable to use at least one selected from among methylcellulose, ethylene glycol, polyol, food oil, and organic fatty acid. Specific examples of the organic binder preferably include hydroxy methyl cellulose or polyvinyl alcohol. Also, the inorganic binder may include those useful in the art, and is not particularly limited, but it is preferable to use at least one selected from among solid silica, solid alumina, solid silica-alumina, silica sol, alumina sol, and water glass. Specific examples of the inorganic binder preferably include fumed silica, silica solution, boehmite, or alumina solution.

The catalyst mixture is typically produced into a catalyst-molded body by coating a catalyst structure such as a honeycomb structure, a monolith structure, etc. with the catalyst mixture, or by directly extruding the catalytic component of the catalyst mixture. Here, the coating and extrusion molding of the catalyst mixture may be easily performed using a method known in the art, and a detailed description thereof is omitted.

Depending on the shape of the produced catalyst-molded body, at least one catalyst-molded body may be disposed in a catalyst-packing portion inside the reactor for direct nonoxidative conversion of methane. The method of disposing the catalyst-molded body therein may also be easily performed using a method known in the art.

Another aspect of the present disclosure pertains to a catalyst for direct nonoxidative conversion of methane, which is prepared using the preparation method described above and includes a catalyst carrier including a catalyst carrier compound and iron dispersed and supported in the form of nanoparticles having an average diameter of 5 nm or less on the catalyst carrier in order to increase the density of the carrier. Here, the form of nanoparticles refers to a form of an active metal supported on the surface of a carrier, and includes a form in which iron, which is an active material, is dispersed in atomic units on the carrier.

The catalyst for direct nonoxidative conversion of methane is in a form in which iron, which is a catalytically active component, is doped in the lattice of a crystalline-molten-state catalyst carrier compound, and the catalyst carrier compound that is used may be silica, alumina, titania, zirconia or silicon carbide, and is preferably silica.

Here, when the average diameter of the iron particles dispersed and supported on the catalyst carrier is 5 nm or less, the density of the carrier is increased by controlling the microstress of the carrier, and the number of defect sites in the carrier is lowered, thereby allowing the methane reaction to proceed efficiently, which is desirable.

For example, when the catalyst carrier compound in the catalyst for direct nonoxidative conversion of methane is silica, there may be provided a structure in which two C atoms and one Si atom are bound to a single Fe atom and embedded in a silica base. Here, the crystal structure of the catalyst carrier is α-cristobalite, which is reversibly converted into β-cristobalite when heated to a temperature of 200° C. to 300° C.

Iron, which is the catalytically active component, is supported in an amount of 0.1 wt % to 10.0 wt %, and preferably 0.3 wt % to 10.0 wt %, based on the total weight of the catalyst. If the amount of iron that is supported is less than 0.1 wt % based on the total weight of the catalyst, the efficiency of direct nonoxidative conversion of methane may be lowered due to the small amount of iron that is capable of acting as a dopant. On the other hand, if the amount thereof exceeds 10.0 wt %, the amount of iron particles, which are active sites of methane activation, may increase, undesirably increasing the rate of coke formation.

The catalyst for direct nonoxidative conversion of methane according to the present disclosure described above allows methane to react with an inert and/or a non-inert gas at a high temperature in the presence of a catalyst to produce olefins and aromatic compounds.

Specifically, the catalyst according to the present disclosure is molded, the catalyst-molded body thus obtained is placed in the catalyst-packing portion of the reactor, and then methane, an inert gas and/or a non-inert gas is introduced thereto.

The methane may be introduced in a volume of 80 to 100% (v/v), and preferably 90 to 100% (v/v), based on the total volume of the gas stream introduced into the reactor, and the inert gas and/or non-inert gas may be introduced in a volume of 20% (v/v) or less, and preferably 10% (v/v) or less, based on the total volume of the gas stream.

The inert gas and the non-inert gas play a role in stably generating and maintaining the reaction state, and the inert gas may be nitrogen, helium, neon, argon, or krypton, and the non-inert gas may be air, carbon monoxide, hydrogen, carbon dioxide, water, monohydric alcohols (C1-C5), dihydric alcohols (C2-C5), or alkanes (C2-C8), and preferably, the inert gas and the non-inert gas are nitrogen and air, respectively.

The reaction temperature may be 900° C. to 1,150° C., and particularly 1,000° C. to 1,100° C., and the pressure may be 0.1 bar to 10 bar, and preferably 0.1 bar to 5 bar, taking into consideration the selectivity and yield of hydrocarbons. Within the above ranges, the selectivity of methane into hydrocarbons may be maximized. Specifically, coke formation is minimized under the above conditions, thereby minimizing the pressure drop due to coke formation during the reaction and the carbon efficiency due to coke formation.

If the reaction temperature is lower than 900° C., the rate of generation of radicals due to methane activation may be low, so energy efficiency may be low, whereas if the reaction temperature exceeds 1150° C., there may occur a problem in which the residence time of methane in the reactor must be minimized in order to suppress coke formation.

The products obtained through direct conversion of methane as described above may include hydrocarbons including paraffins, olefins, and alkynes, such as ethane, ethylene, acetylene, propylene, butylene, etc., and aromatic compounds, such as benzene, toluene, xylene, ethylbenzene, naphthalene, etc.

The method for conversion of methane according to the present disclosure is effective at inducing the activation of methane without precise control of the reaction conditions, minimizing coke formation, and maintaining a stable yield of hydrocarbon compounds even after long-term operation.

A better understanding of the present disclosure may be obtained through the following examples. The following examples are merely set forth to illustrate the present disclosure, and are not to be construed as limiting the scope of the present disclosure.

Example 1

A mixed solution of 375 mL of toluene and 175 mL of methanol was refluxed in an argon atmosphere to remove dissolved oxygen, and then 8.7 g of $FeCl_2$ was added thereto and dissolved. 9.3 g of $NaOC_2H_5$ was added thereto to perform a sol-gel reaction, and 7.9 g of TEOS (tetraethoxysilane) and 10 mL of 0.2 M NaOH were added thereto under reflux conditions, followed by refluxing for 12 hours. The resulting gel was dried for 3 hours in a rotary evaporator, fired at 800° C. for 2 hours in a nitrogen atmosphere, and then washed with distilled water and methanol to obtain fayalite ($Fe_2SiO_4$). 0.056 g of the fayalite thus obtained was subjected to ball milling with 6 g of quartz particles in an Ar atmosphere for 15 hours (at 250 rpm), and then the ball-milled mixture (average diameter: 10 μm) was placed in a reaction furnace [a height-to-diameter ratio (H/D ratio): 0.75] and melted by being heated to 1700° C. at 10° C./min for 6 hours in air. The melt thus obtained was rapidly cooled with water at a speed of 100 K/s, thereby yielding a molten catalyst (0.5 wt % Fe@$SiO_2$) having 0.5 wt % of iron supported thereon.

Example 2

A catalyst was prepared in the same manner as in Example 1 under the conditions shown in Table 1 below. Here, 0.112 g of fayalite was mixed with 6 g of quartz particles, whereby a molten catalyst (1 wt % Fe@$SiO_2$) having 1.0 wt % of iron supported thereon was obtained.

Comparative Examples 1 to 10

Respective catalysts were prepared in the same manner as in Example 2 under the conditions shown in Table 1 below.

TABLE 1

| Classification | Ball mill | | | Melting (fusing) | | Reaction furnace | Catalyst |
| | Speed (rpm) | Time (h) | Melting gas | Temperature (° C.) | Heating rate (° C./min) | H/D ratio* | density (g/cm³) |
| --- | --- | --- | --- | --- | --- | --- | --- |
| Example 1 | 250 | 15 | air | 1,700 | 10 | 0.75 | 2.362 |
| Example 2 | 250 | 15 | air | 1,700 | 10 | 0.75 | 2.358 |
| Comparative Example 1 | 250 | One | air | 1,700 | 10 | 0.75 | 2.355 |
| Comparative Example 2 | 250 | 3 | air | 1,700 | 10 | 0.75 | 2.356 |
| Comparative Example 3 | 250 | 5 | air | 1,700 | 10 | 0.75 | 2.358 |
| Comparative Example 4 | 250 | 15 | air | 1,700 | 5 | 0.75 | 2.368 |
| Comparative Example 5 | 250 | 15 | air | 1,700 | 10 | 4 | 2.225 |
| Comparative Example 6 | 250 | 15 | air | 1,700 | 10 | 0.13 | 2.364 |
| Comparative Example 7 | 450 | One | air | 1,700 | 10 | 0.75 | 2.648 |
| Comparative Example 8 | 450 | 5 | air | 1,700 | 10 | 0.75 | 2.646 |
| Comparative Example 9 | 450 | 8 | air | 1,700 | 10 | 0.75 | 2.630 |
| Comparative Example 10 | 450 | 15 | air | 1,700 | 10 | 0.75 | 2.610 |

*a height (H)-to-diameter (D) ratio of a reaction furnace

[Test Example 1]: Measurement of Physical Particle Properties of Catalyst

Figure 2:
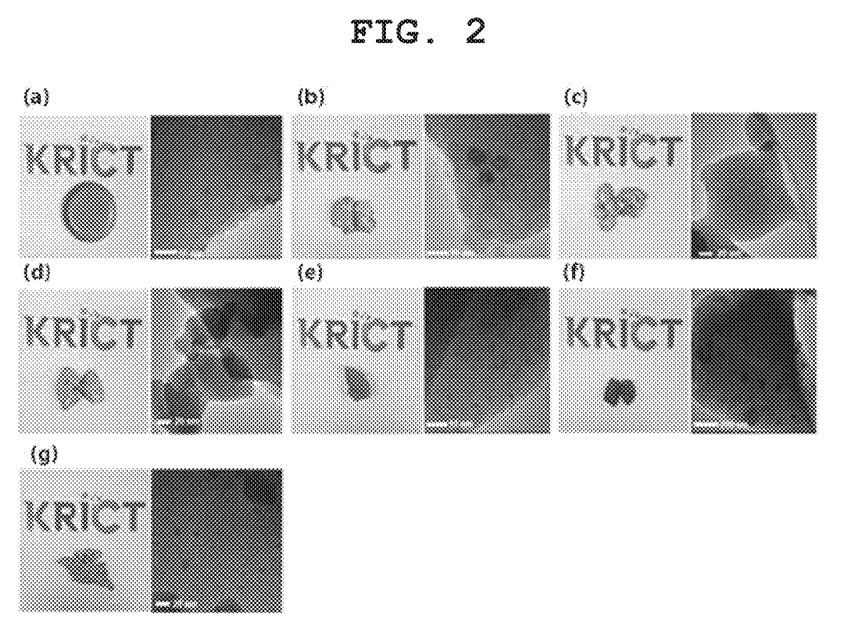
FIG. 2 shows images and TEM images of rapidly cooled melts obtained in Example 1 according to the present disclosure and Comparative Examples 1 to 6, (a) showing Example 1, (b) showing Comparative Example 1, (c) showing Comparative Example 2, (d) showing Comparative Example 3, (e) showing Comparative Example 4, (f) showing Comparative Example 5, and (g) showing Comparative Example 6.

In order to confirm the physical particle properties of the catalysts prepared in Example 1 and Comparative Examples 1 to 6, images and TEM images of the rapidly cooled melts are shown in FIG. 2. In addition, the density of the catalysts prepared in Example 1 and Comparative Examples 1 to 10 was measured using a gas pycnometer (AccuPyc II 1340, Micromeritics), and the results thereof are shown in Table 1. All of the prepared catalysts had a specific surface area of less than 1 $m^2/g$, and were thus confirmed to be compact.

As shown in FIG. 2, the catalyst prepared in Example 1 exhibited increased catalyst uniformity, and also, $\gamma$-$Fe_2O_3$ particles had a size of 3 nm to 4 nm and were uniformly present on the surface of cristobalite. Also, in the case of the catalyst of Comparative Example 5, melted in a reaction furnace having an H/D ratio of 4, and the catalyst of Comparative Example 4, subjected to a heating rate of 5° C./min at the time of melting, Fe metal particles were present therein due to reduction during solidification. Moreover, when the ball mill speed was increased to 450 rpm (Comparative Examples 7 to 10), the catalyst density was increased, but Fe metal particles were present therein due to the reduction of fayalite during ball milling.

[Test Example 2]: Direct Nonoxidative Conversion of Methane 1.2 g of the catalyst prepared in each of Example 1 and Comparative Examples 1 to 3 was packed in a quartz tube reactor (inner diameter: 7 mm). Methane and argon were fed at a volume ratio of 90:10 to perform direct conversion of methane. Here, the gas hourly space velocity was 1,000 $mlg_{cat}^{-1}h^{-1}$, the residence time (gas phase) of gas excluding the catalyst-packing portion was 4.6 seconds (at room temperature), the reaction temperature was 1,000 to 1,040° C., the reaction pressure ($P_{total}$) was 1 bar, and the methane pressure ($P_{CH4}$) was 0.9 bar.

The gaseous hydrocarbons obtained after the reaction were analyzed using a Series 6500 GC made by YL Instrument. The gaseous product was analyzed using a thermal conductivity detector (TCD) connected to a Carboxen 1000 column and two flame ionization detectors (FID) connected with Rt-alumina BOND and RTx-VMS columns. $H_2$, $CH_4$, Ar, $O_2$, CO, and $CO_2$ were separated in the Carboxen 1000 column and detected through TCD, and the conversion rate was calculated by the area of $CH_4$ relative to the area of Ar, which is an internal standard. $C_1$ to $C_6$ light hydrocarbons were separated in the Rt-alumina BOND column and detected through FID, and aromatic compounds were separated in the RTx-VMS column and detected through FID. Through detection of unreacted gases and products, the carbon balance was maintained over 98%. All gases were quantitatively analyzed using standard samples. The coke selectivity was calculated using [Scoke=100–Σproduct selectivity]. The methane conversion rate and the coke selectivity were converted to the reaction rate depending on the reaction temperature. These values were substituted into the Arrhenius equation to determine the apparent activation energy ($E_a$), and the results thereof are shown in FIG. 3.

Figure 3:
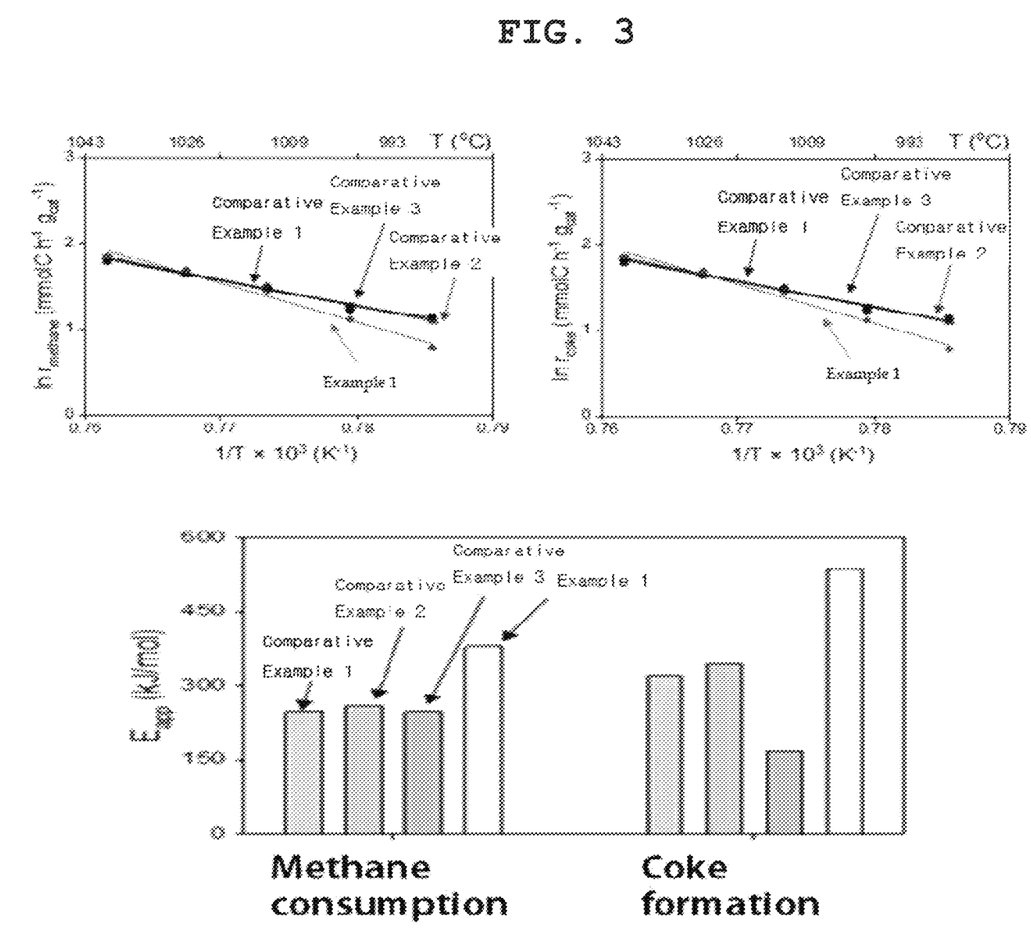
FIG. 3 shows comparison graphs of the apparent activation energy (Ea) of the catalyst for direct nonoxidative conversion of methane prepared in each of Example 1 according to the present disclosure and Comparative Examples 1 to 3.

As shown in FIG. 3, Example 1 exhibited higher activation energy for methane conversion and also relatively higher activation energy for coke formation than the catalysts of Comparative Examples 1 to 3. Specifically, the catalyst prepared in Example 1 was capable not only of stably desorbing methyl radicals that were stably formed on the surface, but also of lowering the coke selectivity, because the rate of excessive dehydrogenation of methane or condensation of secondary products (acetylene, ethylene, and benzene) was low. In addition, the preparation method of the present disclosure makes it possible to selectively promote methane activation by selectively removing defects from the surface of silica and decreasing the distribution of iron cluster particles, which promote coke formation, on the surface.

[Test Example 3]: Measurement of Stability of Catalyst 0.6 g of the catalyst-molded body prepared in Example 1 was placed in a quartz tube reactor (inner diameter: 7 mm). Methane, hydrogen, and argon were fed at a volume ratio of 45:50:5 to perform direct conversion of methane at 1080° C. Here, the gas hourly space velocity was 8000 $mlg_{cat}^{-1}h^{-1}$, the residence time (gas phase) of gas excluding the catalyst-packing portion was 4.33 seconds, the reaction temperature was 1080° C., the reaction pressure ($P_{total}$) was 1 bar, and the methane pressure ($P_{CH4}$) was 0.45 bar. The methane conversion rate and the produced hydrocarbon selectivity were determined in the same manner as in Test Example 2, and the results thereof are shown in Table 2 below and in FIG. 4.

TABLE 2

| Classification | Reaction time (h) | Conversion rate (%) | Selectivity (%) | | | | | |
|---|---|---|---|---|---|---|---|---|
| | | | C2 | C3 | C4 | C5 | Aromatics | Cokes |
| Example 1 | 98 | 5.2 | 88.3 | 2.7 | 2.0 | 0.7 | 6.3 | 0 |

Figure 4:
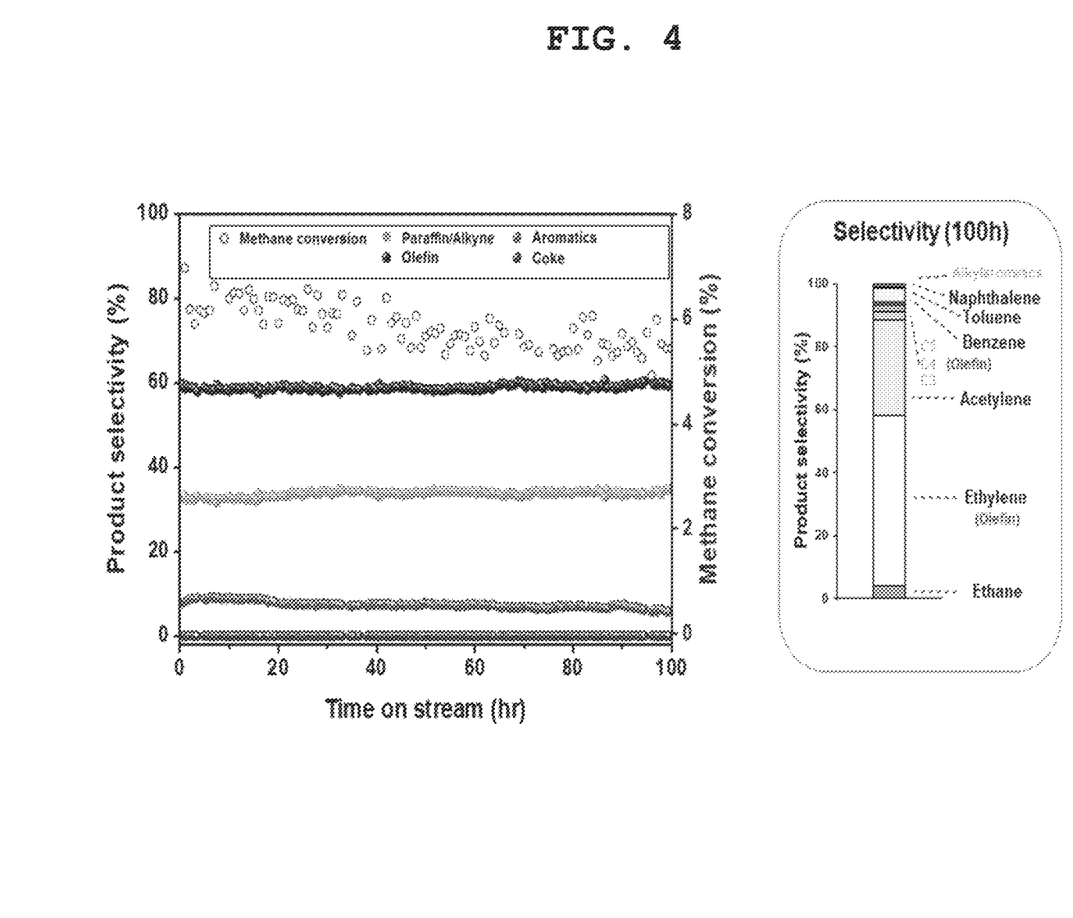
FIG. 4 shows graphs showing the methane conversion rate of the catalyst for direct nonoxidative conversion of methane prepared in Example 1 according to the present disclosure and the product selectivity.

As is apparent from Table 2 and FIG. 4, the catalyst-molded body prepared in Example 1 exhibited stable reaction activity for 100 hours. The methane conversion rate decreased from 6.9% to 4.6% depending on changes in pressure during the reaction. The hydrocarbon selectivity did not exhibit a great difference depending on the reaction time. Here, the C2 hydrocarbon selectivity was 88.3%, and the selectivity of aromatics was about 6.3%. The selectivity of ethane, which is a C2 product, was 3.8%, the selectivity of ethylene was 54.8%, and the selectivity of acetylene was 29.7%. The selectivity of benzene, which is an aromatic compound, was 4.6%, the selectivity of toluene was 0.3%, and the selectivity of naphthalene was 1.2%.

All simple modifications or changes to the present disclosure can be easily implemented by those of ordinary skill in the art, and all such modifications or changes can be considered to be included in the scope of the present disclosure.

The invention claimed is:

1. A method of preparing a catalyst for direct nonoxidative conversion of methane, consisting of:
   (a) mixing fayalite with a catalyst carrier compound to obtain a mixture, and pulverizing for 6 hours to 18 hours at a speed of 100 rpm to 300 rpm in an inert atmosphere using a ball mill;
   (b) placing the pulverized mixture in a reaction furnace having a height-to-diameter ratio of 0.2-3 and then performing melting through heating to a temperature of 1,200°° C. to 2,000° C. at a heating rate of 6° C./min or more to obtain a melt; and
   (c) solidifying the obtained melt.

2. The method of claim 1, wherein in step (a), fayalite is mixed in an amount of 0.1 parts by weight to 20 parts by weight based on 100 parts by weight of the catalyst carrier compound.

3. The method of claim 1, wherein the solidifying in step (c) is performed through rapid cooling at 0.2° C./s to 150° C./s.

4. The method of claim 1, wherein after step (a), steps (b) and (c) are repeatedly performed two or more times.

5. The method of claim 1, wherein the catalyst carrier compound is at least one selected from the group consisting of silica, alumina, titania, zirconia, and silicon carbide.

6. A catalyst for direct nonoxidative conversion of methane, prepared using the method of claim 1 and comprising a catalyst carrier comprising a catalyst carrier compound and iron dispersed and supported in a form of nanoparticles having an average diameter of 5 nm or less on the catalyst carrier.

7. The catalyst of claim 6, wherein the iron is supported in an amount of 0.1 wt % to 10.0 wt % based on a total weight of the catalyst.

8. The catalyst of claim 6, wherein the catalyst carrier is in a molten crystalline state.

9. The catalyst of claim 6, wherein the catalyst carrier compound is at least one selected from the group consisting of silica, alumina, titania, zirconia, and silicon carbide.

* * * * *